United States Patent [19]

Walraven

[11] 4,278,438

[45] Jul. 14, 1981

[54] METHOD AND APPARATUS FOR ANALYSIS OF SACCHARIDES

[76] Inventor: Willem Walraven, P. Lammekensstraat 6, Breda, Netherlands

[21] Appl. No.: 30,734

[22] Filed: Apr. 17, 1979

[30] Foreign Application Priority Data

Apr. 20, 1978 [NL] Netherlands ................... 7804208

[51] Int. Cl.³ ............... G01N 21/00; G01N 31/04; G01N 33/00
[52] U.S. Cl. ................... 23/230 M; 23/230 R; 23/230 PC; 127/36; 127/46 R
[58] Field of Search ............ 23/230 R, 230 M; 422/70; 127/36, 46 R, 46 A

[56] References Cited

U.S. PATENT DOCUMENTS

| | | | |
|---|---|---|---|
| 3,375,080 | 3/1968 | Fuji et al. | 422/70 |
| 3,630,681 | 12/1971 | Arikawa | 422/70 X |
| 3,694,158 | 9/1972 | Lauer et al. | 23/230 R |
| 3,694,160 | 9/1972 | Sagusa et al. | 23/230 R |
| 3,785,864 | 1/1974 | Lauer et al. | 127/46 A |
| 3,806,363 | 4/1974 | Takasaki | 127/46 A |
| 3,817,787 | 6/1974 | Hertzen et al. | 127/46 A X |

Primary Examiner—Michael S. Marcus

[57] ABSTRACT

An accurate new method and a new reagent for the chromatographic preparation and analysis of mixtures of both reducing and non-reducing saccharides is given, the mixture of saccharides being first separated, the oligosaccharides present in the obtained eluate fractions being hydrolyzed to monosaccharides and with the present monosaccharides being reacted with the new reagent to photometricably detectable compounds.

11 Claims, 1 Drawing Figure

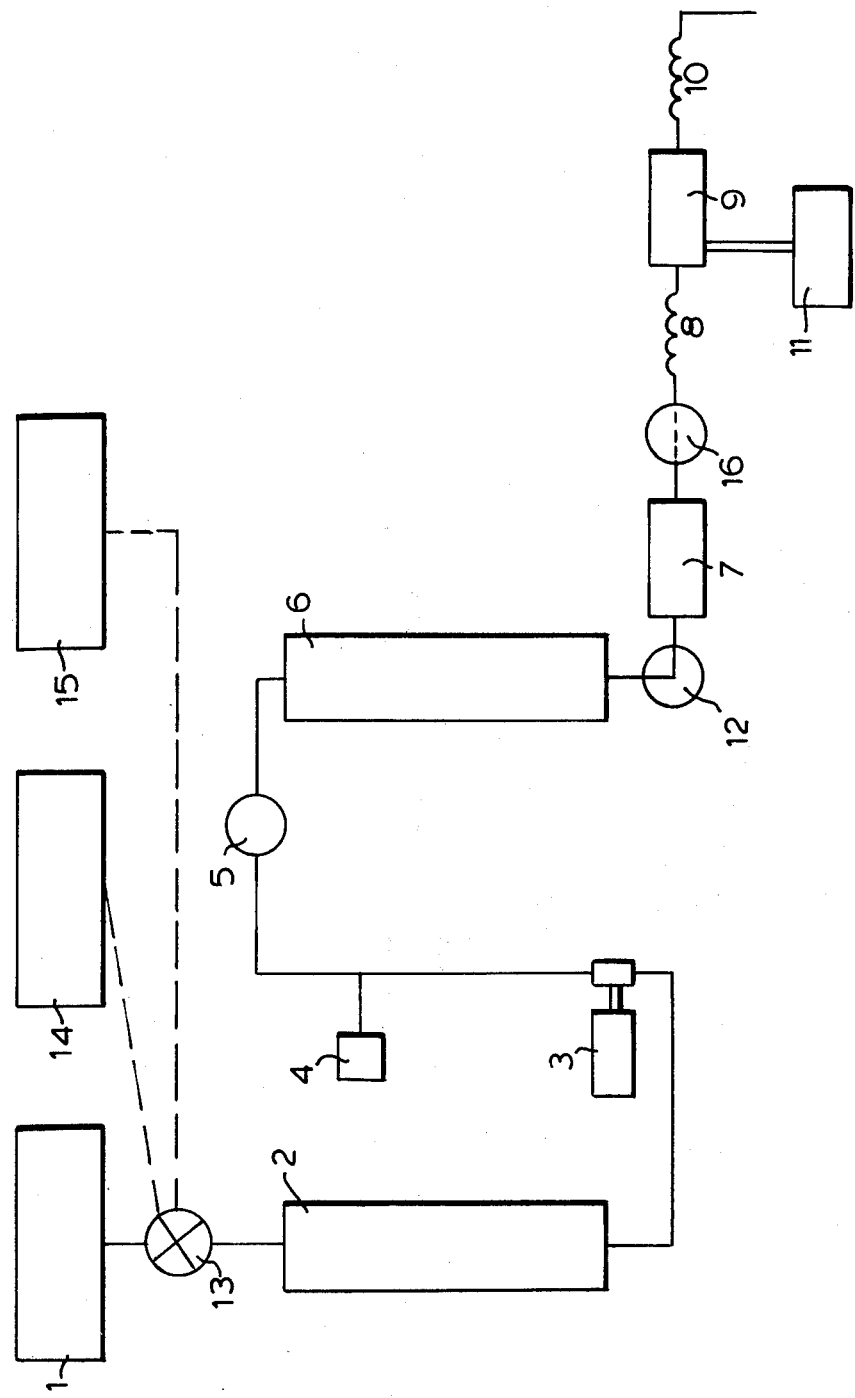

METHOD AND APPARATUS FOR ANALYSIS OF SACCHARIDES

The invention relates to a process for separating and analyzing a mixture of saccharides which comprises making a mixture of these saccharides and/or a reagent and one or a number of buffers flow through a thermally controlled separating column and adding a reagent for monosaccharides to the stream reacting the monosaccharides with the reagent and then detecting the eluate.

A similar process is known generally. See for example, *Analytical Biochemistry*, Vol. 87, pp. 162–168 (1978) and *Journal of Chromatography*, Vol. 156, pp. 354–358 (1978). With the aid of these known processes, however, only mixtures of reducing saccharides can be analyzed, and reagent has to be separately supplied after separation.

It has now been found that mixtures of saccharides containing one or more non-reducing oligosaccharides can be separated and analyzed by using as the reagent, an alkylene polyamine with at least 2 adjacent amino groups and first leading the eluate from the separating column through a reactor in which any oligosaccharides present in the eluate are hydrolyzed and reacting both the monosaccharides present in the original mixture and those formed by hydrolysis with the reagent and then detecting the formed reaction products.

The polyamines to be used as the reagent do not have any aggressive properties, as a result of which the customary detection apparatus can be applied and no special precautions need to be taken. As detection apparatus, use can be made, for example, of fluorometric and photometric devices, the fluorometric ones being especially recommended. With these devices sensitiveness can be achieved in the picomol range with the new process according to the invention.

Ethylene diamine is preferably used as alkylene polyamine.

Although the reagent can be added to the eluate at any place after the separating column and before the reactor, an advantage of the method is that it is possible to lead a mixture of saccharides and one or a number of buffers containing the reagent through the separating column while keeping this column at a temperature lower than 80° C. This combined passage of saccharides, buffers and reagent has the advantage that through this invention the use of an extra pump and lines is avoided, which improves the separation and detection possibilities. By keeping the temperature of the separating column below 80° C. one can avoid the reaction of the reagent with the reducing saccharides in the separating column, which reaction, of course, is undesirable at that point.

In the preferred embodiment the polysaccharides are hydrolized in the hydrolyzer-reactor and the reaction between the monosaccharides and the reagent is activated at the same time, for example by heating, irradiating or with the aid of ultrasound, so that these monosaccharides react with the reagent. The reactor is preferably kept under pressure to prevent boiling at the preferred temperature of between 120° and 180° C.

The invention is now elucidated with the aid of the drawings which depicts a preferred and alternative embodiments of the invention.

From vessel 1 which is filled with the elution agent, a mixture of a buffer, for example a 0.01–0.80 M borate buffer with a pH of between 7.0 and 10.0 and reagent, this elution agent first flows through a purification column 2 in which any impurities present in the elution agent are removed. If a step-wise or continual change of the buffer is necessary, several buffers can be used which, mixed, if required, with the likewise used reagent, are present in the vessels 14 and 15, in which case the buffers(s) are led via cock 13 to the purification column 2.

From column 2 the elution agent is led with the aid of a pump 3 along a device 4 for measuring the pressure to the inlet opening of the sample to be analyzed where 5–100 $\mu$l of this sample, a mixture of saccharides, is injected into the elution agent.

The mixture of the sample to be analyzed and the elution agent is now led through the separating column 6, the temperature of this column is selected between 25° and 80° C., in particular between 50° and 70° C. and is controlled with the aid of a thermostat, in such a way that the sample to be analyzed is separated in the best possible way without the reagent reacting to a considerable extent with the saccharides. With a flow speed of between 20 and 50 ml an hour the pressure-drop over the column is usually between 10 and 25 bars. After this, the stream of eluate fractions is made to flow through reactor 7, which reactor has a temperature between 120° and 180° C. and the pressure-drop over which is 10–12 bars. In this reactor the oligosaccharides present in the reactor hydrolyze and the monosaccharides formed and the monosaccharides already present in the sample at the beginning react with the reagent and form photometrically detectable compounds. The residence time therein ranges between 6 and 8 minutes.

It is also possible to add the reagent to the eluate, for example, at 12 or 16, before or after the reactor respectively. When adding after the reactor the eluate must be kept for about 6–8 minutes at the increased temperature indicated above. Moreover, it is recommended to lead the eluate through coil 8 after the reactor 7; with the aid of this coil the pressure of the eluate, before its being led to the detection device 9, is kept at an increased value and in this the eluate can cool down at the same time. This coil can also be applied after the detection device 9 e.g., at 10.

In the detection device 9 the concentration of the monosaccharides (as reaction product) is measured and the obtained results are, if desired, worked out in an electronic device 11, registered or stored.

EXAMPLE

A degassed 0.6 M borate buffer with a pH of about 9.3 is obtained by adding 30 ml 12 M NaOH to 37.1 g of boric acid in 1 l of water and adds thereto 200 $\mu$l of ethylene diamine. After this elution agent has traversed the purification column, 0.1 ml of a solution of 5 nanomol of sucrose, 5 nanomol of fructose and 5 nanomol of glucose in water are injected therein. This whole mixture is then led with a velocity of 36 ml an hour through a separating column of 6×300 mm of the anion-exchanging resin Durrum DA×4 with a particle size of between 10 and 20 $\mu$m in the borate form with a temperature of 70° C.

The eluate collected from the column is then led with the same speed through the reactor which is kept at a pressure of 10 bars and a temperature of 130° C.

The fluorescence intensity of the obtained reaction products of the separated monosaccharides is continuously measured against the time in the detection device.

It appears that the obtained analysis results correspond with the composition of the saccharide mixture.

The reproducibility of the process to the invention is about 2% in the nanomol range and the sensitivity limit for most saccharides is between 50 and 100 picomol.

With the aid of about 80-100 ml of an isocratic buffer in which the reagent was already present a mixture of about 16 saccharides has been analyzed in a total of two hours with the process of the invention.

It is evident that the new process of the invention can also be used for analyzing compounds related to saccharides.

What is claimed is:

1. A process for separating and analyzing saccharides said process comprising,
    forming a second mixture comprising a mixture of saccharides possibly including oligosaccharides and at least one buffer and a reagent,
    flowing said second mixture through a separating column, and maintaining the temperature of said second mixture below 80° C. whereby premature reactions between said saccharides and said reagents are inhibited,
    hydrolyzing any oligosaccharides present in said second mixture to form monosaccharides,
    reacting with said reagent any monosaccharides originally present in said first mixture and also monosaccharides formed from said hydrolyzing step, and
    detecting the reaction products of said step of reacting.

2. The process of claim 1 wherein said buffer is a borate having a pH in the range from 7.0 to 10.0.

3. The process of claim 1 wherein said reagent comprises an alkylene polyamine having at least two adjacent amino groups.

4. The process of claim 3 wherein said alkylene polyamine is ethylene diamine.

5. The process of claim 1 or 3 wherein said step of maintaining said second mixture below 80° C. further comprises maintaining a temperature of said second mixture above at least 25° C. during said step of flowing said second mixture through the separating column.

6. The process of claim 5 comprising maintaining the temperature of said second mixture between 120° C. and 180° C. during said step of reacting.

7. A process for separating and analyzing saccharides, said process comprising,
    forming a second mixture comprising a first mixture of saccharides possibly including oligosaccharides and at least one buffer and a reagent, said reagent comprising an alkylene polyamine having at least two adjacent amino groups,
    flowing said second mixture through a separating column, and maintaining the temperature of said second mixture below a selected maximum temperature whereby premature reactions between said saccharides and said reagents are inhibited,
    hydrolyzing any oligosaccharides present in said second mixture to form monosaccharides,
    reacting with said reagent any monosaccharides originally present in said first mixture and also monosaccharides formed from said hydrolyzing step, and
    detecting the reaction products of said step of reacting.

8. The process of claim 7 wherein said buffer is a borate having a pH in the range from 7.0 to 10.0.

9. The process of claim 7 wherein said alkylene polyamine is ethylene diamine.

10. The process of claim 7 or 9 wherein said step of maintaining said second mixture below a selected maximum temperature further comprises maintaining the temperature of said second mixture in the range from 25° C. to 80° C. during said step of flowing said second mixture through the separating column.

11. The process of claim 10 comprising maintaining the temperature of said second mixture between 120° C. and 180° C. during said step of reacting.

* * * * *